US012742786B2

(12) United States Patent
Goyal et al.

(10) Patent No.: US 12,742,786 B2
(45) Date of Patent: Sep. 22, 2026

(54) ASSAY AND KIT FOR LIVE ANTIGEN DETECTION AND MONITORING OF NEUROCYSTICERCOSIS

(71) Applicants: Gunjan Goyal, Etawah (IN); Rakesh Sehgal, Chandigarh (IN)

(72) Inventors: Gunjan Goyal, Etawah (IN); Rakesh Sehgal, Chandigarh (IN)

( * ) Notice: Subject to any disclaimer, the term of this patent is extended or adjusted under 35 U.S.C. 154(b) by 934 days.

(21) Appl. No.: 17/953,377

(22) Filed: Sep. 27, 2022

(65) Prior Publication Data

US 2023/0109906 A1 Apr. 13, 2023

(30) Foreign Application Priority Data

Sep. 28, 2021 (IN) ............................ 202111043903

(51) Int. Cl.

| | |
|---|---|
| ***G01N 33/68*** | (2006.01) |
| ***C07K 14/47*** | (2006.01) |
| ***C07K 16/18*** | (2006.01) |
| ***G01N 33/543*** | (2006.01) |

(52) U.S. Cl.

CPC ......... *G01N 33/6893* (2013.01); *C07K 14/47* (2013.01); *C07K 16/18* (2013.01); *G01N 33/54306* (2013.01); *G01N 2470/04* (2021.08); *G01N 2800/26* (2013.01)

(58) Field of Classification Search

None

See application file for complete search history.

(56) References Cited

PUBLICATIONS

Zhang et al. Antigenicity, Immunogenicity, Allergenicity. Allergy Bioinformatics. Nov. 3, 2015;8:175-86. (Year: 2015).*

UniProt—Q8MPE0 (original web page https://www.uniprot.org/uniprotkb/Q8MPE0/entry) (Year: 2025).*

GenBank: CAD21536.1 embl accession AJ428468.1 putative lysine-rich protein, partial [Taenia solium] Jul. 24, 2016.

Rodriguez S, Wilkins P, Dorny P. Immunological and molecular diagnosis of cysticercosis. Pathogens and global health. Sep. 1, 2012;106(5):286-98.

Nash TE, Garcia HH. Diagnosis and treatment of neurocysticercosis. Nature Reviews Neurology. Oct. 2011;7(10):584-94.

(Continued)

*Primary Examiner* — Rebecca M Giere

*Assistant Examiner* — Alexander Alexandrovic Volkov

(74) *Attorney, Agent, or Firm* — Trupti P. Joshi

(57) ABSTRACT

The present invention broadly relates to the field of proteomics, bioinformatics & immunology for detection of Neurocysticercosis (NCC). More specifically, the present invention relates to an in vitro immunoassay for the diagnosis of active neurocysticercosis in biological samples. Further, the present invention relates to the identification of a novel antigen comprising of 219 amino acids of Putative lysine rich protein (PLRP) 25 kDa and its use in the detection of Neurocysticercosis. The amino acid sequences of antigenic polypeptides TSPP21 and TSPP22 are provided, polypeptides are useful as detection tool for identification of *T. solium* for recognizing active antigens in biological samples. In broad spectrum the invention defined here provides method for detecting active antigen in serum and urine of neurocysticercosis patients in kit formulation. In solitary cyst cases and cases where diagnosis is not clear by neuroimaging, this test will be helpful.

2 Claims, 13 Drawing Sheets

Figure 1:
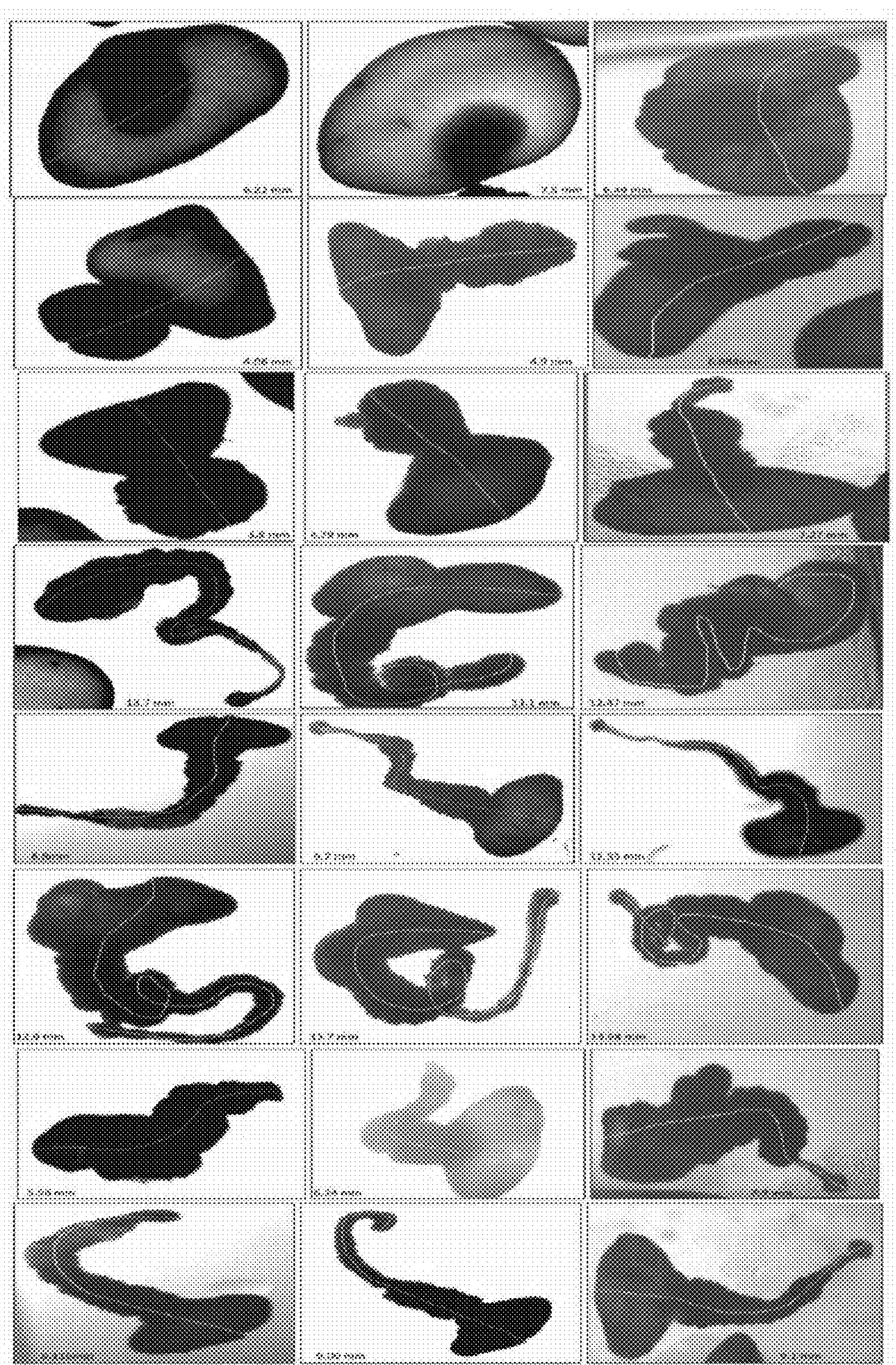

Specification includes a Sequence Listing.

SEQ ID NO:1

MKGKMTIGAVSEPSKKHKKSSEFGNGGQATEEGSQPSGRKRKTRP
TESNESRATEVITEAEAFRPTKRRKKSLEVAIDSTEERKAVSHWQQ
KSERDLEKSKKNVTETKKPESVKKSVKFADELVAPRSLPKNKSKT
SILKVSTPSVKASNENSGVEKANEADGNGTETKARKPKKSKNALK
RIRWVKRHHKKTFSRRQRRANRELARSRPQRDAEQHLA

SEQ ID NO: 2

CSQPSGRKRKTRPTESNESR

SEQ ID NO: 3

RQRRANRELARSRPQRDAEC

(56) References Cited

PUBLICATIONS

Menikou S, McArdle AJ, Li MS, Kaforou M, Langford PR, Levin M. A proteomics-based method for identifying antigens within immune complexes. Plosone. Dec. 23, 2020;15(12):e0244157.
Wang H, Cai Q, Liang Y, Shui J, Tang S. A simple and high-throughput luciferase immunosorbent assay for both qualitative and semi-quantitative detection of anti-HIV-1 antibodies. Virus research. Apr. 2, 2019;263:9-15.
Gholipour A, Moosavian M, Makvandi M, Galehdari H, Alvandi A, Mard SA. Development of an indirect sandwich ELISA for detection of urinary antigen, using Legionella pneumophila PAL protein. World Journal of Microbiology and Biotechnology. May 2014;30(5):1463-71.

* cited by examiner

FIG. 10

SEQ ID NO:1

MKGKMTIGAVSEPSKKHKKSSEFGNGGQATEEGSQPSGRKRKTRP
TESNESRATEVITEAEAFRPTKRRKKSLEVAIDSTEERKAVSHWQQ
KSERDLEKSKKNVTETKKPESVKKSVKFADELVAPRSLPKNKSKT
SILKVSTPSVKASNENSGVEKANEADGNGTETKARKPKKSKNALK
RIRWVKRHHKKTFSRRQRRANRELARSRPQRDAEQHLA

SEQ ID NO: 2

CSQPSGRKRKTRPTESNESR

SEQ ID NO: 3

RQRRANRELARSRPQRDAEC

| | 1 | 2 | 3 | 4 | 5 | 6 | 7 | 8 | 9 | 10 | 11 | 12 | |
|---|---|---|---|---|---|---|---|---|---|---|---|---|---|
| A | -0.001 | 0.001 | 0.551 | 0.266 | 0.007 | 0.223 | 0.267 | 1.938 | 1.466 | 1.472 | 0.45 | 0.404 | Blank 450 |
| B | 0.876 | 0.563 | 0.281 | 0.257 | 0.21 | 0.235 | 0.255 | 0.236 | 0.308 | 0.326 | 0.249 | 0.379 | Blank 450 |
| C | 0.347 | 0.212 | 0.25 | 0.286 | 3.236 | 3.527 | 0.247 | 0.24 | 2.373 | 2.651 | 0.32 | 0.409 | Blank 450 |
| D | 0.161 | 0.191 | 0.219 | 0.264 | 2.125 | 2.099 | 3.402 | 3.493 | 0.265 | 0.336 | 0.368 | 0.698 | Blank 450 |
| E | 0.416 | 0.389 | 0.258 | 0.263 | 3.602 | 3.453 | 3.499 | 3.612 | 0.201 | 0.355 | 0.243 | 0.253 | Blank 450 |
| F | 0.178 | 0.161 | 0.268 | 0.222 | 2.188 | 1.365 | 0.324 | 0.282 | 0.329 | 0.308 | 0.61 | 0.649 | Blank 450 |
| G | 0.254 | 0.133 | 1.69 | 1.807 | 2.897 | 2.973 | 3.274 | 3.111 | 0.382 | 0.35 | 0.21 | 0.204 | Blank 450 |
| H | 0.217 | 0.117 | 0.467 | 0.54 | 3.507 | 3.515 | 0.379 | 0.514 | 0.515 | 0.516 | 0.191 | 0.2 | Blank 450 |

FIG. 12B

ASSAY AND KIT FOR LIVE ANTIGEN DETECTION AND MONITORING OF NEUROCYSTICERCOSIS

CROSS REFERENCE TO RELATED APPLICATION

This application claims the benefit of priority to Indian Patent Application Number 202111043903, filed on Sep. 28, 2021, the contents of which are hereby incorporated by reference in their entirety.

REFERENCE TO SEQUENCE LISTING

This application is being filed electronically via EFS-Web and includes an electronically submitted sequence listing in the XML format. The XML file contains a sequence listing entitled "FP10679_SeqList_ST26" created on Sep. 27, 2022 and having a size of ~4 KB. The sequence listing contained in this XML file is part of the specification and is incorporated herein by reference in its entirety.

FIELD OF THE INVENTION

The present invention broadly relates to the field of proteomics, bioinformatics & immunology. More particularly, the present invention relates to an assay and kit for semi-quantitative detection of a target. Putative lysine rich protein (PLRP) for detection of active Neurocysticercosis (NCC).

BACKGROUND ART

Neurocysticercosis is considered to be the commonest helminthic CNS infestation. It is a neglected parasitic disease and is a grave health issue especially in developing countries. Neurocysticercosis (NCC) is a leading cause of epilepsy, responsible for active epilepsy in endemic countries, it manifests with myriad of symptoms. Seizures are most common manifestation of symptomatic NCC and occur in most of cases. However, not all people with Neurocysticercosis (NCC) infestation of brain, manifest with seizures and a proportion of people with cysticercus infestation of the brain, might remain asymptomatic. Till date, there are no definite clinical or laboratory findings which can prognosticate future course of seizures in patients with Neurocysticercosis (NCC), though variable course of seizures have been documented in literature. This disease is being increasingly recognized due to ingestion of *Taenia* eggs through contaminated food and water. Food home burden epidemiology reference group reported 2.8 million disability adjusted life years. Even in the United States each year approximately 2000 NCC patients get hospitalized and in countries endemic for NCC number of patients continually increase. In developing countries like India with large areas in farming, people of villages generally defecate in open fields, which leads to spread of parasite eggs and finally contaminate food and water of environment.

Diagnosis of Neurocysticercosis (NCC) is based on "Del Brutto criteria" which is mainly based on neuroimaging, (Del Bruno et al., 2001). Conventionally, CT & MRI are the neuroimaging procedures which are used for diagnosing Neurocysticercosis. These tests are useful to determine if cystic lesions are present or not in the patient samples, to determine whether the patient is suffering from the disease. Despite decades of research to develop sensitive diagnostic tests, diagnosis of NCC relies on MRI & CT, but they are too expensive to be afforded by people in developing countries. Till now the end points for Neurocysticercosis (NCC) therapy are not defined.

The data obtained from neuroimaging are not always proportional to the severity of the disease, neuroimaging information is morphological in nature, not functional. In final stages of evolution during therapy, cysts may not appear in MRI or CT, and discontinuation of therapy is ordered if the cysts do not appear in the MRI scans.

Another drawback of these conventional tests was observed when hydrocephalous condition is present in patients. This condition obstructs the CT & MRI and hence a poor prognosis can be made as the cysts are not detectable.

One approach for diagnosis of the disease would be to identify the circulating antigens in hydrocephalous patients, which would be greatly helpful for diagnosis of Neurocysticercosis (NCC), and such patients can receive anti-parasite treatment which effectively kills cysticerci in ventricles & subarachnoid region. Antigen based tests based on HP10 and HP6 antibodies developed in mice by injecting antigens from viable cysts and were screened against lentil lectin glycoproteins from *Taenia saginata* cysts has limitation that, when cysticerci are found in the subarachnoid space or ventricles, HP10 can be identified, but not when they are found in the parenchyma and solitary cysts cases (Bobes et al., 2006; Garcia et al., 2000; Harrison et al., 1989). B158 & B60 antibodies against *Taenia saginata* viable cysticerci excretory secretory antigens (ESAs), commercial version of B158 test apDia kit available in the United States, apDia kit available has also limitation as it has very less sensitivity in case with solitary cysts and also this test is costlier (Castillo et al., 2009).

In Indian subcontinent, where solitary cysticercus granuloma accounts in 60% cases antigen tests are important for the diagnosis of the disease (Kumar Garg et al., 2000; Prabhakaran et al., 2007; Rajshekhar et al., 1991). Further, the apDia kit is not based on specific antigen detection, which is non homologous to *Homo sapiens* and secondly this kit is costlier.

Antibody based tests are available, but antibodies detected in samples may indicate previous exposure to infection not necessarily active infection in patient, resulting in a transitory antibody response or due to living in endemic zones.

The choice of diagnostic tests is important; it should be effective and can be used even in low resource settings for the detection of the disease. Solitary lesion is the most common presentation which results in seizures, and it is most important to differentiate it from other infections, vascular lesions and tumors. Anti-cysticercal antibody detection by ELISA (Enzyme linked Immunosorbent Assay) has a high rate of false positives and is not recommended as a diagnostic criterion for Neurocysticercosis (NCC).

However, a problem faced with antigen-based tests is that the antigen remains hidden in the immune system of host, and hence the conventional tests that were previously developed had a higher sensitivity for patients with multiple cysts in comparison to solitary cysts. Accordingly, there is a need to develop a non-invasive antigen detection test which would help in saving patients from unnecessary treatment. This will be an exceptional tool for the management of neurocysticercosis patients clinically.

Therefore, the inventors of the present invention have developed an antigen-based test for the diagnosis of Neurocysticercosis disease in patients with solitary cysticercous granuloma. As reported by Gomez et al. (2015), *Taenia solium* is unable to synthesize the amino-acid lysine and secreted proteins contain enzymes able to degrade lysine-containing peptides. The inventors of the present invention have for the first time identified Putative lysine rich protein (PLRP) for active detection of Neurocysticercosis. Thus, putative lysine rich protein is a potential degradation product resulting from complex host-*Taenia solium* interaction and it is detected in patient's biological samples only during the stage of active infection of the disease.

SUMMARY

The present invention broadly relates to the field of proteomics, bioinformatics & immunology for diagnosis of Neurocysticercosis (NCC). The present invention relates to an in-vitro immunoassay for the detection of active neurocysticercosis in biological samples. Further, the present invention relates to the identification of a novel antigenic sequence comprising of 219 amino acids of Putative lysine rich protein (PLRP) and its use in the diagnosis of Neurocysticercosis. The inventors of the present invention have for the first time identified Putative lysine rich protein (PLRP) for active detection of Neurocysticercosis. Putative lysine rich protein is a potential degradation product resulting from complex host-*Taenia solium* interaction and it is detected in patient's biological samples only during the stage of active infection of the disease. The present invention also provides methods and kits along with instruction manual for diagnosis of NCC. Invention relates to novel antigenic fragment sequences of putative lysine rich protein (PLRP), TsPP21 and TsPP22 and their use in the development of the sandwich AgELISA test developed which has the ability to detect the existence of living cysts in biological samples of patients and animals, making it a distinctive test.

OBJECTIVES OF THE INVENTION

An important objective of the present invention is to provide an assay for detecting the presence of a target Putative lysine rich protein (PLRP).

Another objective of the present invention is to provide a kit for detecting the presence of a target Putative lysine rich protein (PLRP).

Still another objective of the present invention is to provide a novel antigenic sequence comprising of 219 aa of Putative lysine rich protein (PLRP).

A further objective of the present invention is to provide a method for semi-quantitative as well as qualitative detection of a Putative lysine rich protein (PLRP) antigen.

BRIEF DESCRIPTION OF THE FIGURES AND TABLES

The accompanying drawings illustrate some of the embodiments of the present invention and together with the descriptions, serve to explain the invention. These drawings have been provided by way of illustration and not by way of limitation. The components in the drawings are not necessarily drawn to scale, emphasis instead being placed upon clearly illustrating the principles of the aspects of the embodiments.

FIG. 1: Changes in the size of *T. solium* recorded by stereomicroscopy at 15, 30 and 60 day.

Figure 2:
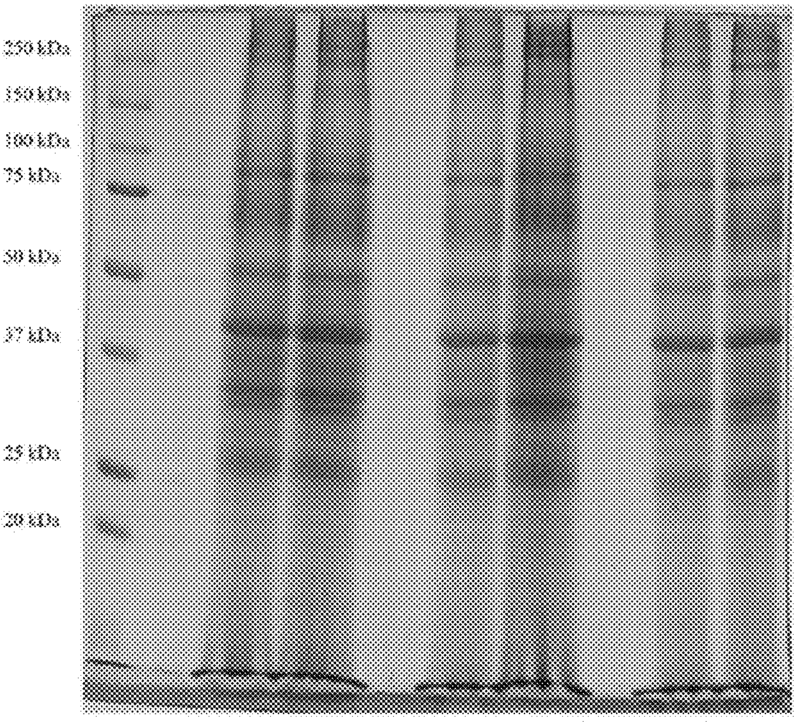

FIG. 2: SDS-PAGE of *T. solium* crude antigens Lane 1—MW marker, Lane 3, 4, 6, 7, 9, 10—crude antigen (20 μg).

Figure 3:
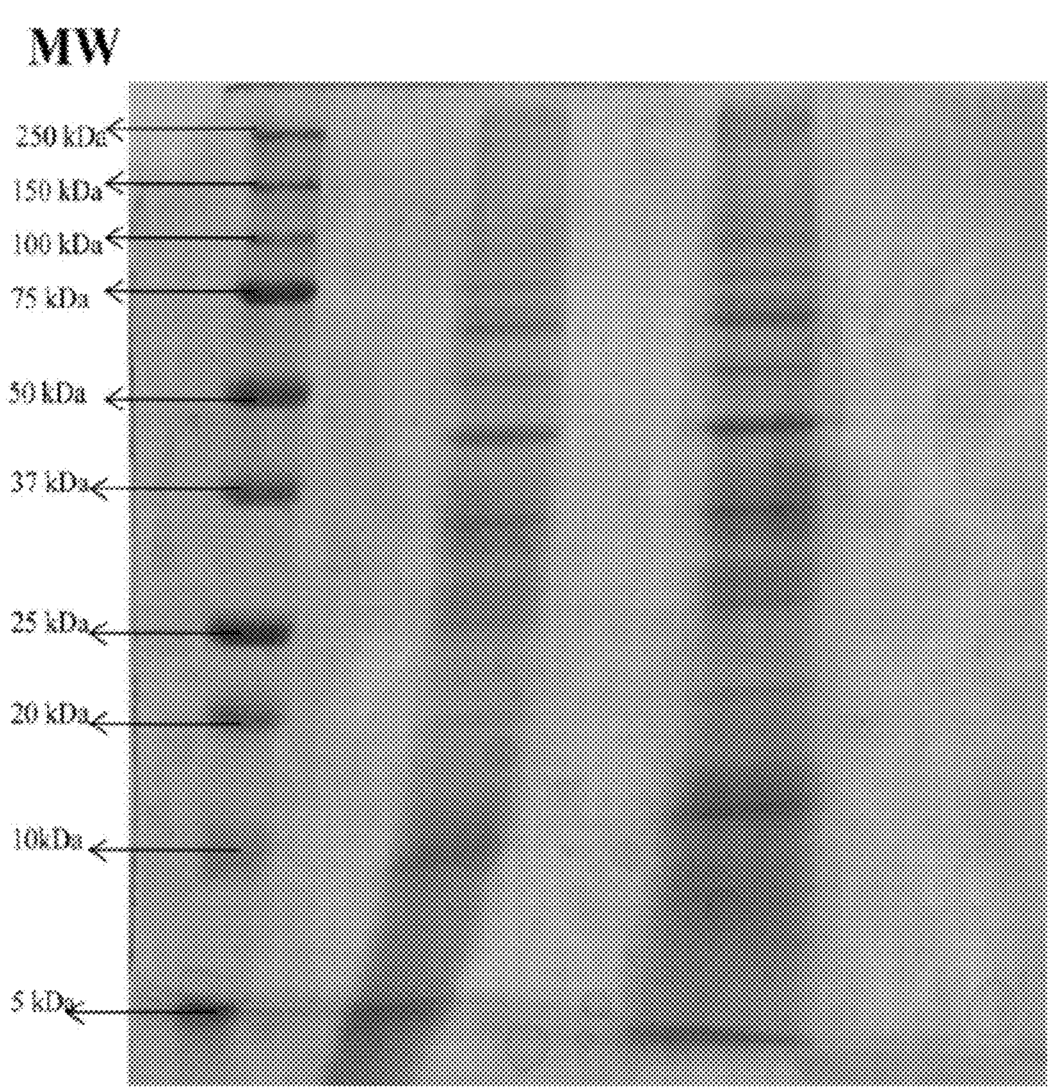

FIG. 3: SDS-PAGE of *T. solium* low molecular weight antigens Lane 1—molecular weight marker, Lane 3—LMW antigen (20 μg), Lane 5—LMW antigen (30 μg).

Figure 4:
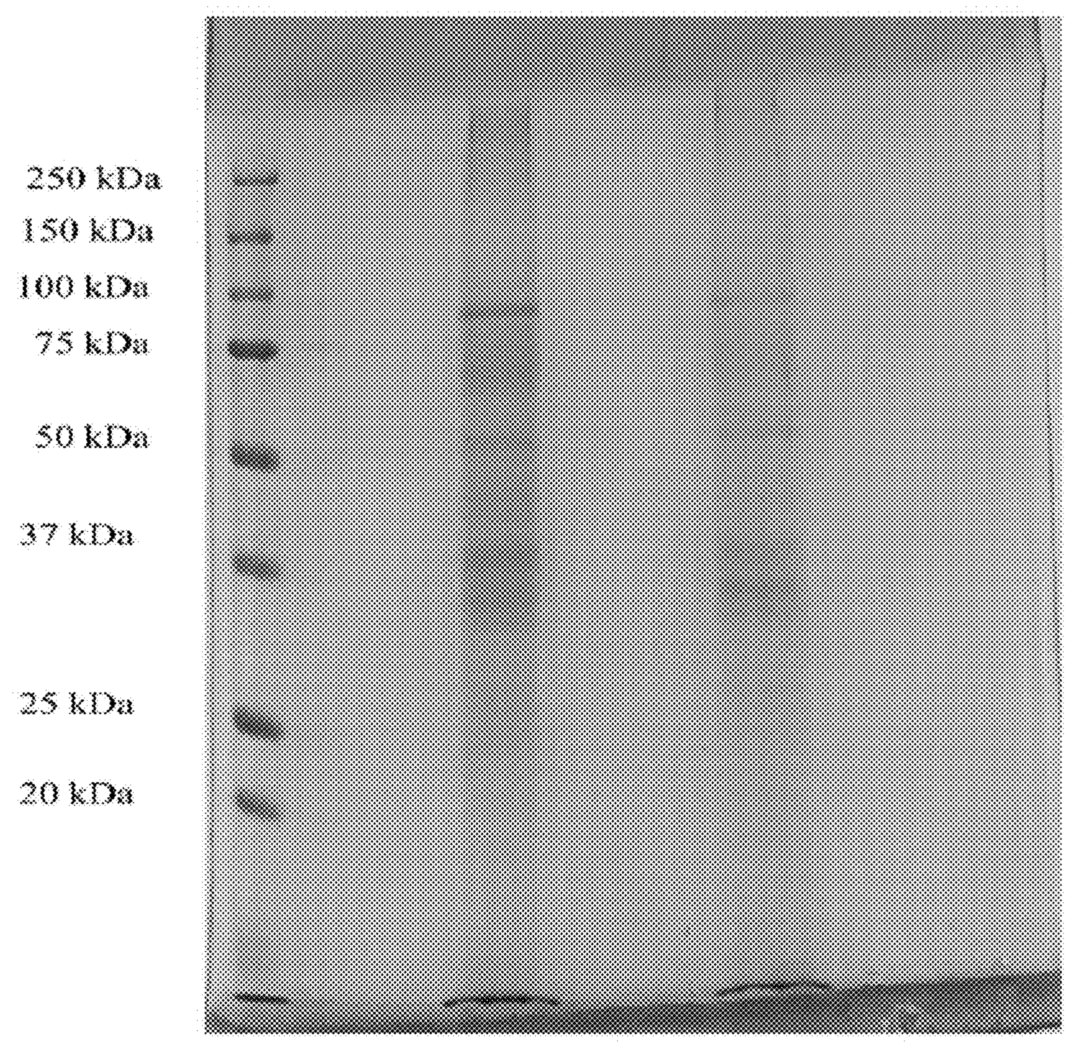

FIG. 4: SDS-PAGE of *T. solium* excretory secretory antigens Lane 1—MW marker, Lane 3—ES antigen (30 μg), Lane 5—ES antigen (20 μg).

Figure 5A:
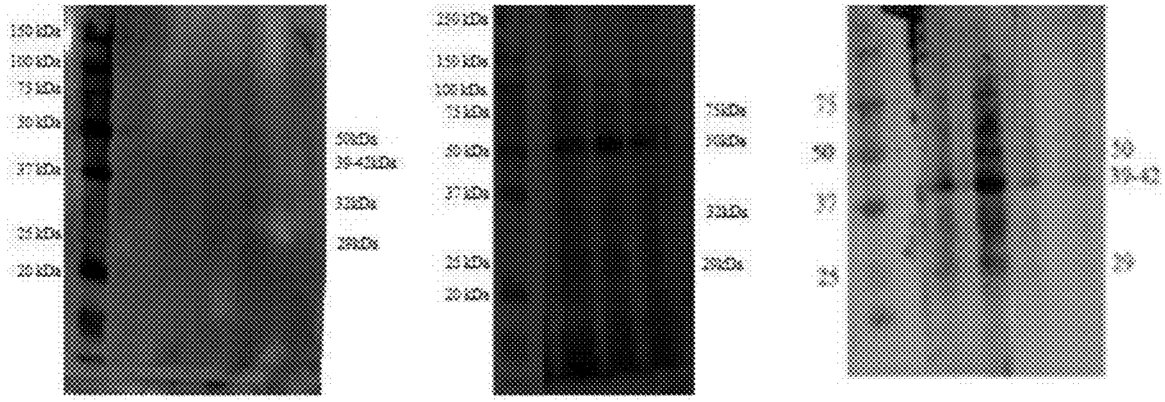

FIG. 5A: Immunoblotting of *T. solium* cyst protein extracts interacted with a pool of NCC samples, SDS-PAGE was run with 40 μg of cyst protein fraction using 12% gels. The gels were blotted onto NCM. Chemiluminescence kit was used to detect the antigen-antibody response (a) Serum (b) CSF(c) Urine.

Figure 5B:
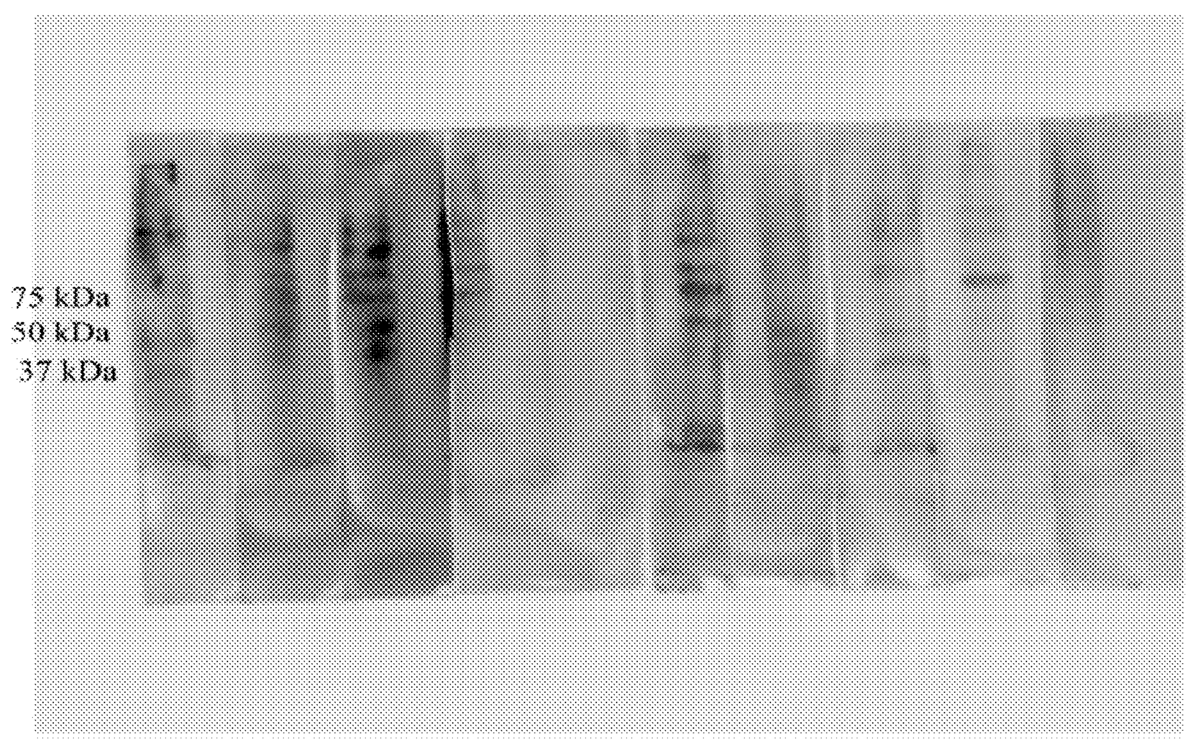

FIG. 5B: Immunoblotting of *T. solium* cyst crude antigen interacted with serum samples, SDS-PAGE was run with 40 μg of crude antigen fraction using 12% gels. The gels were blotted onto NCM. Chemiluminescence kit was used to detect the antigen-antibody response. 39, 50, 75 kDa bands were detected.

Figure 6:
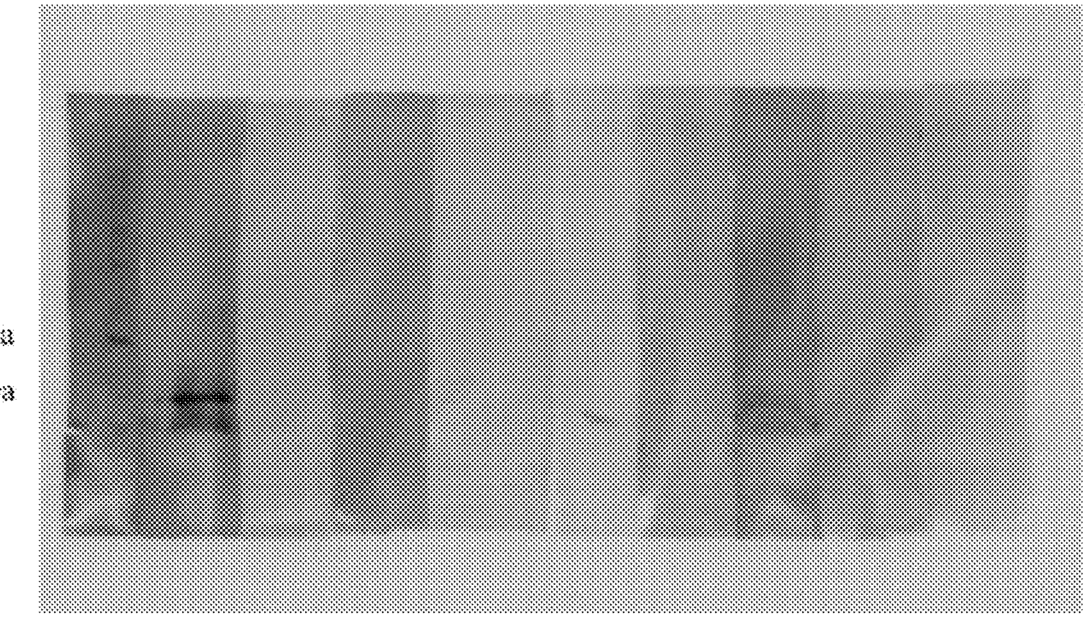

FIG. 6: Immunoblotting of LMWA extracts of *T. solium* reacted with serum samples from neurocysticercosis patients. 40 μg of LMWA protein was resolved by SDS-PAGE using 12% gels, the gels were blotted onto NCM. Chemiluminescence kit was used to detect the antigen-antibody response. 10 kDa band was detected.

Figure 7:
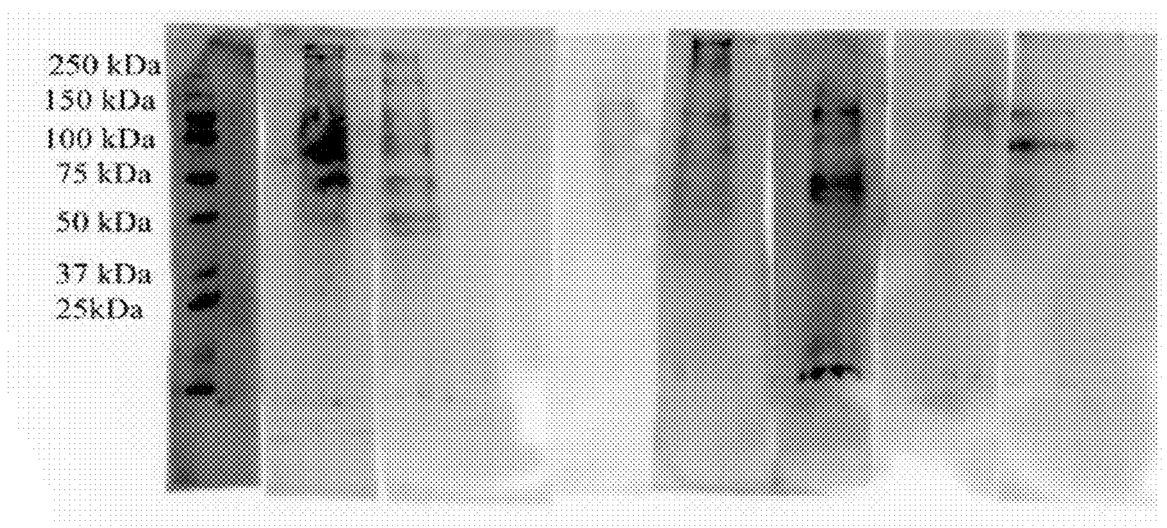

FIG. 7: Immunoblotting of ESA extracts of *T. solium* cysts reacted with serum samples from neurocysticercosis patients. 40 μg of ESA protein was resolved by SDS-PAGE using 12% gels, the gels were blotted onto NCM. Chemiluminescence kit was used to detect the antigen-antibody response. 58, 67 and 87 kDa bands were detected.

Figure 8:
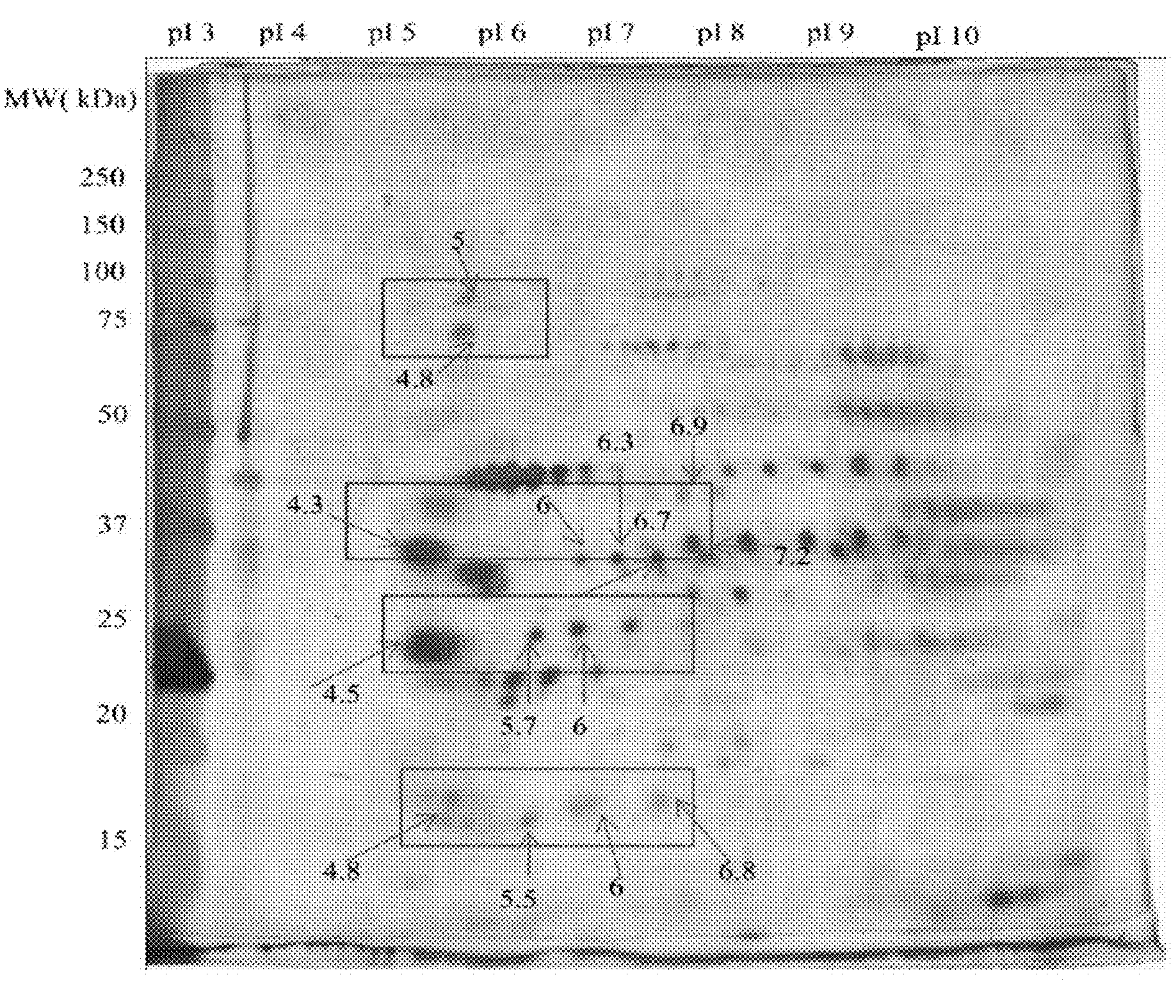

FIG. 8: 2D-PAGE identification of *T. solium* cysticercus immunoreactive proteins on silver-stained gel. Highly immunogenic fractions were obtained 16, 17, 18, 25, 27, 32, 37, 67 and 75 kDa. Innumerable proteins were obtained between 4-7 pI.

Figure 9:
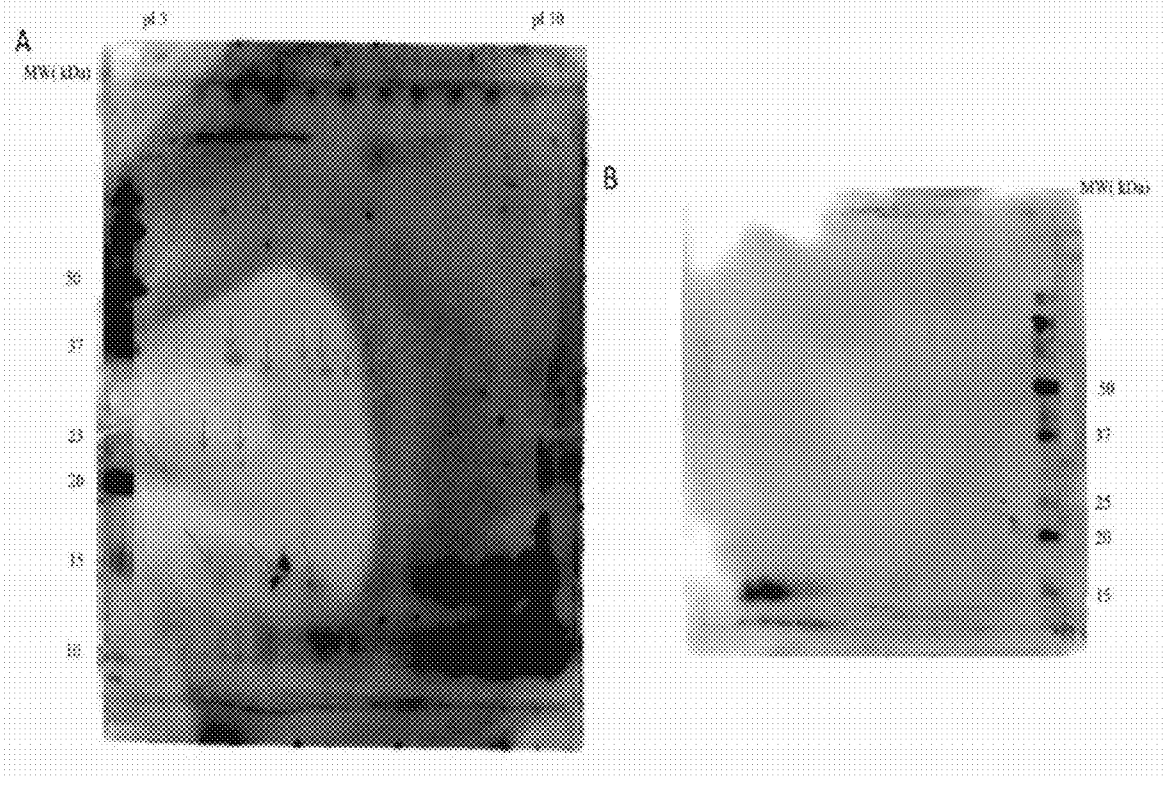

FIG. 9: Identification of *T. solium* immunoreactive proteins by 2D-PAGE western blot. The gels were blotted onto nitrocellulose membrane and reacted with pool of serum samples. Chemiluminescence kit was used to detect the antigen-antibody response (panel A) Western blots from NCC patients (panel B) Western blots from controls.

Figure 10:
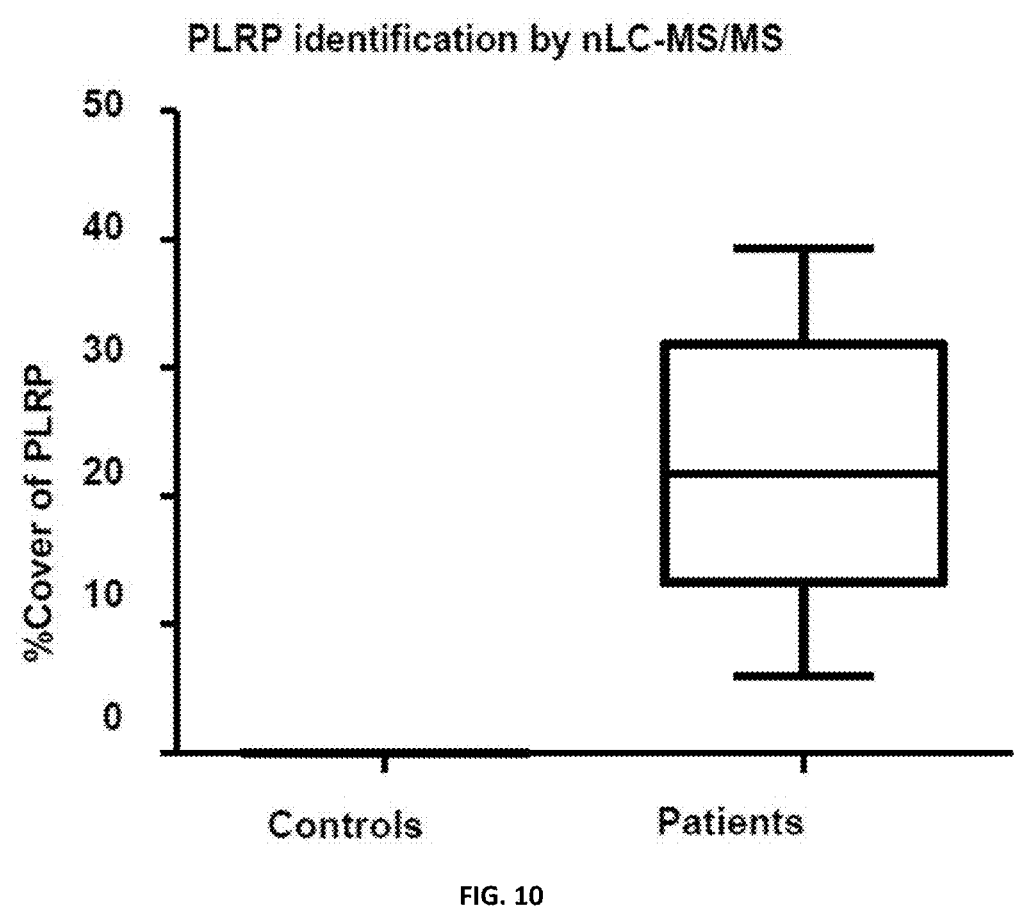

FIG. 10: Box plot of level of PLRP identification by nLC-MS/MS in patients.

Figures 11, 12A:
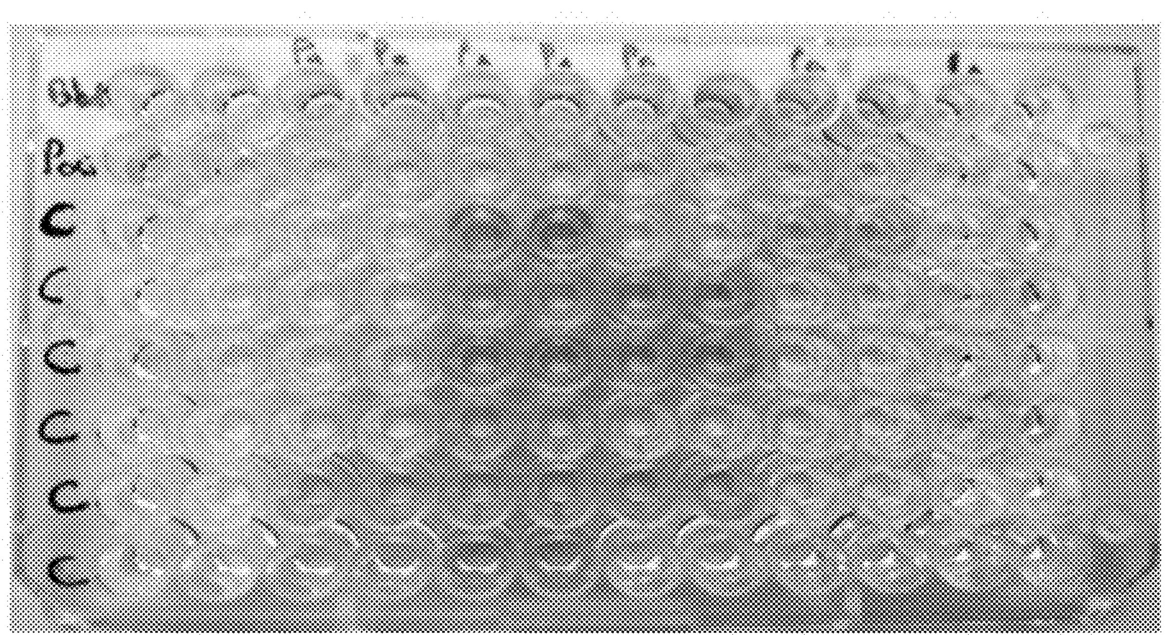

FIG. 11: Sequence listing (SEQ ID NO. 1, 2 and 3) for Putative lysine rich protein (PLRP) and two highly antigenic fractions TsPP21 and TsPP22.

FIG. 12A: Ag detection using the sandwich ELISA as exemplified by the present invention ELISA plate.

FIG. 12B: OD readings of plate at 450 nm.

Figure 13:
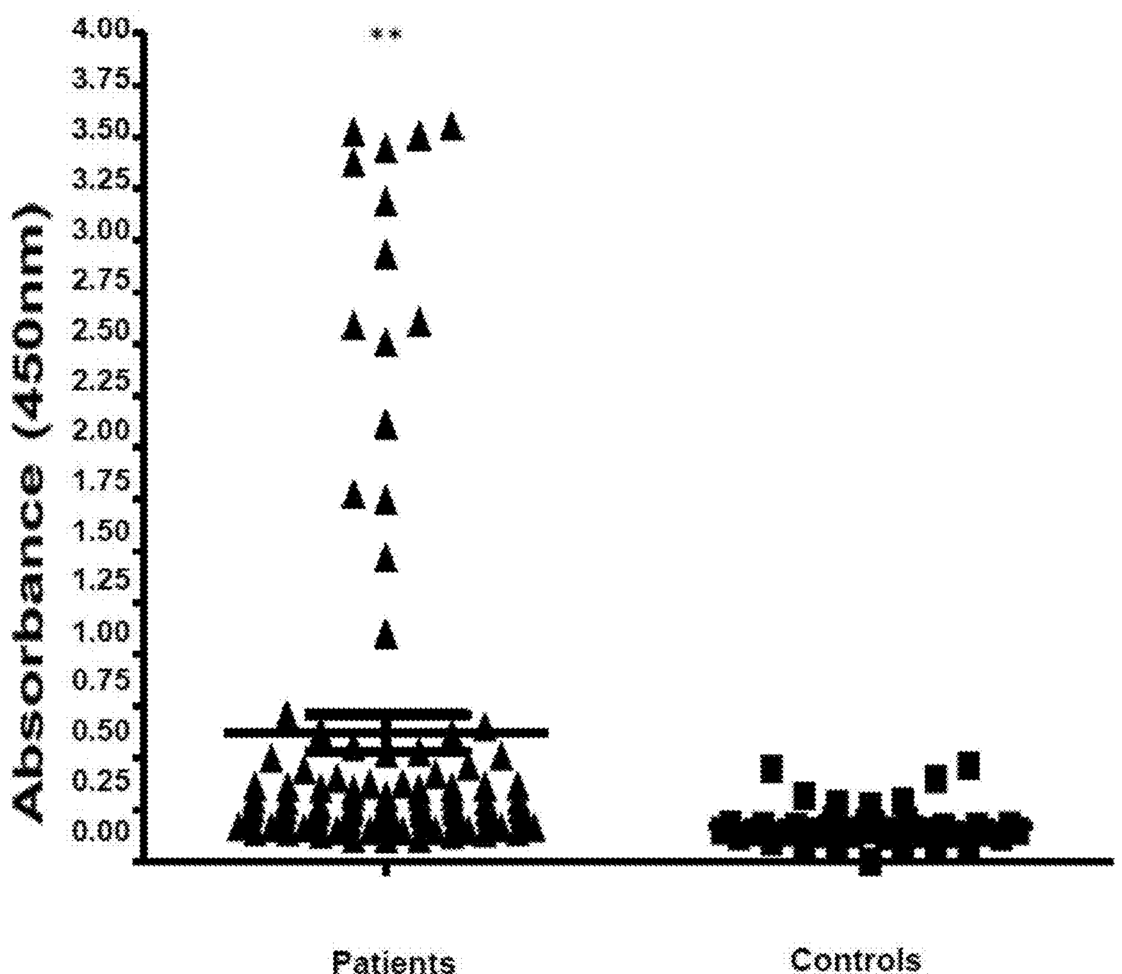

FIG. 13: Scatter plot of level of PLRP detected by ELISA in the serum of NCC patients (103) and control (40) subjects ** $P<0.002$, 't' test.

Figure 14:
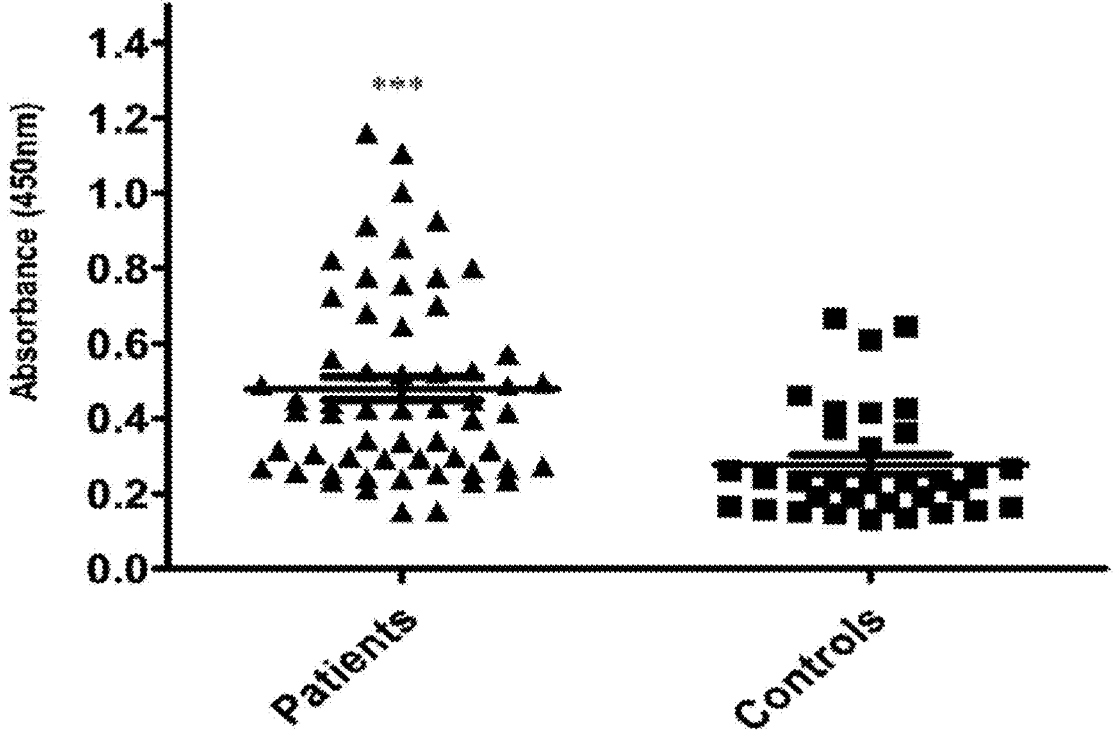

FIG. 14: Scatter plot of Level of PLRP detected by ELISA in the urine of NCC patients (59) and control (33) subjects. *** $P<0.0001$ 't' test.

Figure 15:
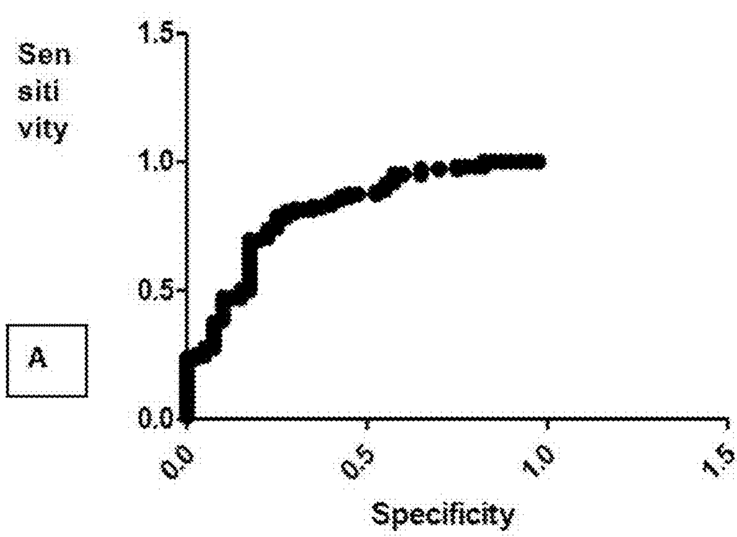
Figure 15:
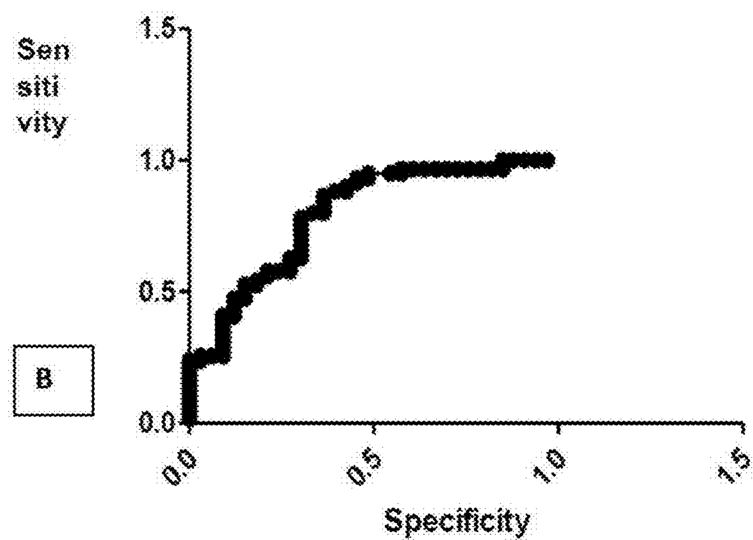

FIG. 15: Receiver Operator Statistics (ROC) curve graph—Serum (panel A); Urine (panel B).

Table 1: PLRP identification cover percentage chart in 10 patient samples (serum-P2, P3, P4, P6, P8; urine-PU12, PU13; CSF-Pcs1, Pcs5; cyst-PC9).

Table 2: ELISA (Serum) validation in different stages.

Table 3: ELISA (Urine) validation in different stages.

Table4: ELISA results and validity of assay in Serum & Urine.

DETAILED DESCRIPTION OF THE INVENTION

At the very outset of the detailed description, it may be understood that the ensuing description only illustrates a particular form of this invention. However, such a particular form is only exemplary embodiment, and without intending to imply any limitation on the scope of this invention. Accordingly, the description is to be understood as an exemplary embodiment and teaching of invention and not intended to be taken restrictively.

Unless defined otherwise, technical and scientific terms used herein have the same meaning as commonly understood by one of ordinary skill in the art to which this invention belongs. Further, unless otherwise required by context, singular terms shall include pluralities and plural terms shall include the singular.

Definitions

The use of "comprise", "comprises", "comprising", "contain", "contains", "containing", "include", "includes", and "including" are not intended to be limiting. It is to be understood that both the foregoing general description and this detailed description are exemplary and explanatory only and are not restrictive.

A "subject" in the context of the present invention is intended to include living organisms in which cysticercosis can occur.

The terms "treatment", "treating", "treat" and the like are used herein to generally mean obtaining a desired pharmacologic and/or physiologic effect. The effect may be prophylactic in terms of completely or partially preventing a disease or symptom thereof and/or may be therapeutic in terms of a partial or complete cure for a disease and/or adverse effect attributable to the disease.

"Treatment" as used herein covers any treatment of a disease in an animal or mammal, particularly a human, and includes:

(a) preventing the disease or symptom from occurring in a subject which may be predisposed to the disease or symptom but has not yet been diagnosed as having it;
(b) inhibiting the disease symptom, i.e., arresting its development; or
(c) relieving the disease symptom, i.e., causing regression of the disease or symptom.

Unless otherwise defined, scientific and technical terms used herein shall have the meanings that are commonly understood by those of ordinary skill in the art. Further, unless otherwise required by context, singular terms shall include pluralities and plural terms shall include the singular.

The foregoing broadly outlines the features and technical advantages of the present disclosure in order that the detailed description of the disclosure that follows may be better understood. It should be appreciated by those skilled in the art that the conception and specific embodiment disclosed may be readily utilized as a basis for modifying the disclosed methods or for carrying out the same purposes of the present disclosure.

The present invention is the result of identification of an active antigen in patients suffering from Neurocysticercosis that could be used for diagnosis of active disease in biological samples. The inventors of the present invention have for the first time identified Putative lysine rich protein (PLRP) for active detection of Neurocysticercosis. Thus, PLRP is a potential degradation product resulting from complex host-*Taenia solium* interaction and it is detected in patient's biological samples only during the stage of active infection of the disease. The inventors of the present invention proved that PLRP was not detected in excretory secretory antigen collected from the culture of cysts at different days for ninety days. The culture was maintained for more than ninety days, the growth of cysts to tapeworm stage was recorded by using stereomicroscopy and Evos FL auto microscope under in-vitro conditions (FIG. 1).

This unique antigen has been found in circulation in patients suffering from Neurocysticercosis in active stage, and under normal circumstances PLRP antigen is not present in human body unless the human has acquired the Neurocysticercosis (NCC) infection.

Accordingly, a major objective of the present invention was to develop a diagnostic test which can determine the presence of PLRP in a biological sample, which can be an indicator of active Neurocysticercosis (NCC).

The distinction between active and inactive Neurocysticercosis (NCC) is more significant in clinical terms than the distinction between Neurocysticercosis (NCC) and no Neurocysticercosis (NCC), since the presence or absence of live cysts can affect treatment decisions. Thus, the present invention is highly useful as it can detect live infection and it can be carried out in biological samples such as serum and urine samples.

An added advantage of the present invention is that serum samples are obtained by venipuncture which is minimally invasive and urine which can be easily collected. In contrast, the extraction of CSF samples relies on painful procedure and can only be obtained in hospital infrastructure, only by trained medical practitioners.

Thus, the exploration of PLRP will help to provide basis for following the therapeutic targets and patient will not to have to suffer from irrelevant cysticercidal therapy. Accordingly, the present invention is an exceptional tool for the management of neurocysticercosis patients clinically. *Taenia* antigen detection aims to provide suitable information about disease activity, in a more sensitive way, antigen release is related to inflammatory activity, and that inflammatory activity is related to the clinical activity of the disease. *Taenia* antigen detection in the biological samples is correlated with NCC immunological active phase. Further, there has never been a large-scale proteomics study of *Taenia solium* before comprising of antigens and biological samples which could give a promising test.

Development and advances of the high-throughput proteomics screening technologies have revolutionized the field of Parasitology. The present study used two proteomics approaches to gain a better understanding of the disease. Despite all challenges, proteomics can provide rapid high-throughput analysis of proteins on a large scale, significantly contributing to unravelling key protein-protein interactions, discovering signaling networks, and understanding disease mechanisms. One dimensional and two-dimensional gel electrophoresis helps to understand maximum fifty percent of proteome because some proteins cannot be obtained in gel due to physiochemical properties (hydrophobicity) or because they are present in very low concentrations, so in the present invention multistep separation techniques are used in different types of antigens and biological samples. In general, bottom-up proteomics requires proteolytically digested proteins extracted from any biological sample, followed by the liquid chromatographic (LC) separation of the resulting peptides that are eluted and subjected to electrospray ionization. This was carried out by using 'in-gel digestion' and 'in-solution' digestion in the proteomics of *Taenia solium*. Further, 'in-solution' digested depleted serum, urine and CSF samples were identified using nLC-MS/MS for proteomics study of NCC patients. Putative lysine rich protein (PLRP) was the unique protein identified by nLC-MS/MS.

The diagnostic test of the present invention has the added advantage that the sensitivity and specificity is much better than any other antigen detection tests available for human biological samples. Further, the presently described diagnostic test is also economical in comparison to other tests available in the market. For instance, the presently described diagnostic kit can be prepared and sold for a minimum amount of Rs, 300/test which is substantially lower than the price of the already available kits which are priced in the range of 1160 euro (1,02,997 Rs plus taxes extra) for 96 tests. Hence, the present invention provides an easy, economical, minimal y invasive approach for detection of Neurocysticercosis.

The novel discovery of the circulating antigen in the sera of patients suffering from the active disease is beneficial as until now the antigenic sequence has not been used anywhere around the world for detection of active Neurocysticercosis. The sandwich AgELISA test developed has the ability to detect the existence of living cysts in biological samples of patients, making it a distinctive test.

Further, the inventors of the present invention discovered that PLRP has reasonable sensitivity and specificity and monitoring of PLRP antigen level, with antibodies produced against TsPP21 and TsPP22 antigenic fragments, will help in determining proper management and effective anti-cysticercidal therapy to be given to patients.

In an embodiment of the present invention, the present invention provides an assay for qualitative and semi-quantitative detection of a target Putative lysine rich protein (PLRP) defined by the SEQ ID NO: 1 or any antigenic fragments thereof in a test sample, comprising:

i. providing a reaction vessel, coated with a capture antibody onto its surface;
ii. adding a test sample comprising the target antigen into the reaction vessel to facilitate binding between the bound antibody and the target antigen;
iii. washing the solid substrate in the reaction vessel to remove any excess, target antigen not bound to the solid substrate;
iv. introducing the detection antibody into the reaction vessel to facilitate binding between the target molecules bound to the capture antibody and the detection antibody;
v. washing the solid substrate in the reaction vessel to remove any excess detection antibody not bound to the target molecule; and
vi. quantifying the amount of sandwiched target antigen by the presence of aggregated detection antibody-target antigen-capture antibody based on measurement of optical density.

In another embodiment, the target antigen putative lysine rich protein (PLRP) is detected in active neurocysticercosis patient's biological samples.

In still another embodiment, the highly antigenic fragment sequences of the PLRP are TsPP21 and TsPP22 defined by SEQ ID NO: 2 and 3.

In yet another embodiment, the test sample is a biological fluid selected from serum, urine, cerebrospinal fluid, saliva and cysts.

In a further embodiment, the present invention provides an antibody capable of binding to a target Putative lysine rich protein (PLRP) defined by SEQ ID NO: 1 or an antigenic fragment thereof.

In another embodiment, the antibody of the present invention is capable of specifically binding to an antigenic fragment defined by SEQ ID NO: 2 or 3.

In a further embodiment, the present invention provides a kit for qualitative and semi-quantitative detection of a target Putative lysine rich protein (PLRP) defined by the SEQ ID NO: 1 or any antigenic fragments thereof in a test sample, the kit comprising:

i. a capture antibody for capturing a target antigen;
ii. a detection antibody that binds specifically to an epitope of the target PLRP antigenic sequence;
iii. a positive control containing the antigen;
iv. a negative control tacking antigen;
v. a means for collecting and adding a sample; and
vi. an instruction manual.

In yet another embodiment, the assay or kit of the present invention can be used for detecting Neurocysticercosis and its severity in a subject.

In another embodiment, the present invention provides an antigenic sequence comprising of 219 aa long fragment of Putative lysine rich protein (PLRP) defined by the SEQ ID NO: 1.

In yet another embodiment, the present invention provides antigenic fragment sequences TsPP21 defined by SEQ ID NO: 2 and TsPP22 defined by SEQ ID NO: 3.

In a further embodiment, the Putative lysine rich protein (PLRP) can be used in preparation of a vaccine or as target for drug development or for targeting cysticercosis and taeniasis.

Without limiting the scope of the present invention as described above in any way, the present invention has been further explained through the examples provided below.

EXAMPLES

Example 1: Identification of Proteins in the Antigens and Biological Samples The detailed analysis of low molecular weight antigen and excretory/secretory proteins of *Taenia solium* using SDS-PAGE and Nano-scale liquid chromatographic tandem mass spectrometry (nLC-MS/MS) were carried out.

Materials and Methods i. Samples

*Taenia solium* cysts were cultured and excretory secretory antigen (ESA) was collected. ESA, low molecular weight antigens and patient's samples were subjected to Nano-scale liquid chromatographic tandem mass spectrometry (nLC-MS/MS).

The study was carried out in Medical Parasitology Department, Postgraduate Institute of Medical Education and Research (PGIMER), Chandigarh, India. One hundred and three human subjects suffering from Neurocysticercosis and forty controls were included in the study after taking written informed consent as per the guidelines of the Institute Ethical Committee.

Serum, CSF and urine samples of confirmed NCC patients (5 to 50 years) were collected. Two groups of subjects were included in the present study.

A) Group A: NCC patients confirmed by using clinical, radiological and MB criteria, n=103 (serum n=103, CSF n=5 and urine n=59)
B) Group B: Controls, n=40
B1: Seven patients suffering from tuberculosis
B2: Thirteen patients proven for other parasitic diseases (toxoplasmosis, Hydrated etc.)
B3: Three patients proven for other noninfectious neurological diseases B4: Seventeen healthy controls (serum and urine)

(CSF was not collected separately and was only used when drawn for other routine tests.)

ii. Processing of the Samples

CSF—For each patient, lumbar puncture was performed and 2 ml of CSF was collected, samples were centrifuged at 2000 rpm for 10 min to eliminate cells and other insoluble materials and CSF was stored in polypropylene tubes at −80° C. until analysis.

Serum—For separation of serum, each blood sample (7 ml) was kept for 1 h at 37° C. to clot. The clot was loosened carefully from the sides of the tube. The serum was centrifuged for 20 minutes at 4° C. at 4000 rpm, and the supernatant was kept at −20° C. until further use.

Urine—Urine was collected in sterile uricoll containers and centrifuged at 10,000 rpm 20 min at 4° C. and the supernatant just above the pellet were collected and stored at −20° C.

*T. solium* cysts were obtained from naturally infected slaughterhouse pigs, cysts excised and extracted from infected pork and inspected under a microscope for *T. solium* larva confirmation. The cysts were cleaned in phosphate buffered saline (pH 7.4), (PBS) supplemented with 2 mM phenyl methyl sulfonyl fluoride (PMSF), streptomycin (0.1 mg/ml) and penicillin (100 units/ml). The cysts were then suspended in normal saline with 2 mM PMSF and homogenized in a homogenizer at 4° C. (S. R. V. Atluri et al., 2009). This was followed by sonication (Soni prep 150 MSE 332 sonicator) 8 min at 12 kHz (60 sec on and 30 sec off). The sonicated samples were centrifuged for 30 min 30,000 g at 4° C., Clear supernatant were used as the crude extract and kept in −70° C. Protein concentration was calculated using the Lees and Paxman technique (Lees and Paxman, 1972).

Lower molecular mass antigenic fractions (LMM) (8-30 kDa) were prepared by amicon 0.5 ml filters from Merck Millipore (30 kDa and 3 kDa).

Cysticerci were collected from pig infected with Cysticerci cysts. *T. solium* cysticerci selected with intact larva and with fluid containing translucent bladder were selected. Microscopy of cysts was done for the confirmation of *T. solium* larva. RPMI-1640 (Gibco) media was used, to which 2 mg antifungal amphotericin B, 20 mg/L cefotaxime, 5 mg/L fungizone, 2 mg/L gentamycin and 100 mg/L penicillin were added and filtered with membrane filter (0.2 μm pore size). All procedures were done in a laminar hood. Cysticerci were washed and cultured in flasks containing the medium, incubated for 24 h at 37° C. in 5% $CO_2$ After every 48 hrs medium was replaced, medium removed was collected and further supernatant of culture were centrifuged for 10 min at 25,000 rpm at 4° C. Protease inhibitors of sigma were used containing 130 μM bestain, 10 μM pepstatin, 1 μM leupeptin, 0.2 μM aprotitin, 1 μM phosphoramidon and 2 μM AEBSF. During the duration of culture, cysts showed morphological changes. Development of larva was monitored with stereo zoom microscopy at 15, 30 and 60 days. Excretory secretory products from developmental stages of *T. solium* were all stored in −80° C. until use.

iii. Determination of the Antigenicity of Identified Antigenic Fragments

Using pools of serum samples, 2 antigenic peptides 50 and 39-42 kDa were obtained by EITB, while 75, 50, 29 kDa antigenic bands were strongly developed in pools of CSF and 50, 39-42 and 29 kDa bands were obtained in urine pool samples (FIG. 5*a*). The immunoreactive bands recognized by antibodies from sera of patients were 39, 50, 62.5, and 96 kDa obtained in crude antigen (FIG. 5*b*). While in low molecular weight antigen immunoreactive specific bands obtained with sera of patients were at 10 kDa (FIG. 6). In ESA, immunoreactive bands obtained with serum sample were at 58, 67, and 87 kDa (FIG. 7).

iv. EITB Detection on 2D

Comparison of silver-stained gel and western blot of 2D developed with serum samples of patients helped in locating antigenic spots. Innumerable proteins were detected on gel between 25 kDa and 37 kDa with pI 4-7 (FIG. 8), with serum samples these antigenic spots were immunoreactive. Highly immunogenic proteins obtained between pI 4-7 at 16 kDa, 17 kDa, 18 kDa, 25 kDa, 27 kDa, 32 kDa, 36 kDa, 67 kDa, and 75 kDa (FIG. 9). 16 spots reacted with patients' sera in western blotting. Antigenic fraction at 27 and 36 kDa were more immunogenic (FIG. 9, panel A). Blot developed with controls sample did not showed spot (FIG. 9, panel B).

v. Identification of the Antigenic Proteins in the Biological Samples by nLC-MS/MS Nine spots were obtained with LMWA (Low molecular weight antigen) in 1D-PAGE which reacted with patient's sample. LMWA in solution digested samples and *T. solium* developed in culture, when they were subjected to nLC-MS/MS, total 409 protein entries were obtained, from which 349 protein entries were related to genus *Taenia*, which consisted of total 184 unique proteins. Eight spots obtained from excretory secretory antigen and six in-solution digested samples of ESA collected from culture at every tenth day during the culture were subjected to nLC-MS/MS, 209 protein entries were obtained, from which 181 protein entries were related to *Taenia*, and it consisted of 121 unique proteins. Comparative analysis of proteins identified by nLC-MS/MS in LMWA and ESAs resulted in 221 common proteins.

Fifteen biological neurocysticercosis samples were subjected to nLC-MS/MS, among them seven serum samples (live vesicular cysts, one colloidal and one multiple foci predominantly calcified), three urine (two colloidal and one vesicular), three CSF (two vesicular cysts and one multiple cysts predominantly vesicular) and two human cysts samples (Cystic lesion) were there. Total 1366 protein entries were obtained, out of which 1163 were related to *Taenia*, and it consisted of 294 unique proteins.

Unique proteins obtained in patients' samples, were compared with unique proteins obtained in both LMWA and ESA and a total of 123 unique accession numbers were found. To identify the molecular functions, cellular components and biological processes of the antigenic proteins found in LMWA, ES and biological samples of patients, GO analysis was carried out using Gene Ontology database. Comprehensive 84 unique common proteins were found after considering the common antigen names, gene and molecular weight. While in the five controls serum samples (two healthy controls, two tuberculosis and one trichinella) presence of only 13 proteins out of the 84 unique proteins was displayed, these 13 expressed proteins did not fulfill the BLASTP criteria because they displayed significant similarity with *Homo sapiens.*

BLASTP was performed of these 123 protein entries against *Homo sapiens* and thus 25 proteins which have no significant similarity with *Homo sapiens* were obtained. 18 out of 25 proteins shared common Pfam PF05596. This Pfam consists of several common antigens from *Echinococcus* and *Taenia* families.

Comprehensive proteomic analysis of these 25 proteins revealed that apart from putative lysine rich protein (PLRP) which was present in ten out of fifteen samples, the other 24 proteins displayed their presence in one to five samples only.

Among 15 biological samples subjected to n-LC MS/MS, 10 biological samples in which PLRP was obtained, 5 were serum (4 vesicular, 1 multiple foci predominantly calcified), 2 urine (one of each vesicular and colloidal), 2 CSF (one multiple predominantly vesicular and other colloidal) and one sample of human cyst (Table 1).

Other proteins common in blood, CSF and human cyst samples were putative lysine rich protein (*Taenia solium*), annexin B3, c-Fos (*Taenia crassiceps*), fascilin-1 (*Taenia solium*), oncosphere protein Tso22a (*Taenia solium*), oncosphere protein Tso22b (*Taenia solium*). Serpin (*Taenia solium*), c-Jun (*Taenia crassiceps*), fascilin-2 (*Taenia solium*), H-17g protein tegumental antigen (*Taenia solium*), Rec name full sodium/potassium transporting ATPase subunit alpha.

TABLE 1

PLRP identification cover percentage chart in 10 patient samples (serum-P2, P3, P4, P6, P8; urine-PU12, PU13; CSF-Pcs1, Pcs5; cyst-PC9)

| % Cover | Accession no. | Protein name | Species | Sample ID |
|---|---|---|---|---|
| 31.96 | CAD21536.1 | putative lysine-rich protein, partial [*Taenia solium*] | *Taenia solium* | P2 |
| 23.74 | CAD21536.1 | putative lysine-rich protein, partial [*Taenia solium*] | *Taenia solium* | P3 |
| 39.27 | CAD21536.1 | putative lysine-rich protein, partial [*Taenia solium*] | *Taenia solium* | PCs5 |
| 16.89 | CAD21536.1 | putative lysine-rich protein, partial [*Taenia solium*] | *Taenia solium* | P8 |
| 5.94 | CAD21536.1 | putative lysine-rich protein, partial [*Taenia solium*] | *Taenia solium* | PC9 |
| 12.79 | CAD21536.1 | putative lysine-rich protein, partial [*Taenia solium*] | *Taenia solium* | PCs1 |
| 10.96 | CAD21536.1 | putative lysine-rich protein, partial [*Taenia solium*] | *Taenia solium* | PU12 |
| 22.83 | CAD21536.1 | putative lysine-rich protein, partial [*Taenia solium*] | *Taenia solium* | PU13 |
| 14.61 | CAD21536.1 | putative lysine-rich protein, partial [*Taenia solium*] | *Taenia solium* | P4 |
| 38.36 | CAD21536.1 | putative lysine-rich protein, partial [*Taenia solium*] | *Taenia solium* | PCs5 |
| 31.51 | CAD21536.1 | putative lysine-rich protein, partial [*Taenia solium*] | *Taenia solium* | P6 |
| 20.55 | CAD21536.1 | putative lysine-rich protein, partial [*Taenia solium*] | *Taenia solium* | PC9 |

Accordingly, based upon the dominant presence of PLRP in maximum number of biological samples of patients, it was selected for further validation by Sandwich Ag ELISA assay. Further, the inventors of the present invention identified two (FIG. 11) highly antigenic fractions, TsPP21 and TsPP22, of 19 amino acids each from PLRP, upon comprehensive study of the hydrophilicity, hydrophobicity, surface probability, antigenicity and disordered scores by bioinformatics software BepiPred, ABCpred, LBtope, SVMTriP, imed, BcePred. Further, additional cysteine was added at N'-Terminal and C'-Terminal of the respective epitopes in these antigenic fragments for Keyhole Limpet Haemocynin (KLH) conjugation. The selected epitopes had good antigenicity and surface probability. The antigen PLRP is highly antigenic protein, having antigenicity of about 80%.

Accordingly, the antigenic epitopes were recognized through bioinformatics software, antibodies raised against these epitopes were purified and labeled with biotin and used as capture and detection antibodies for developing Sandwich ELISA to detect active infection in patients. After identification of the unique antigenic protein, this protein was used to develop an antigen-based sandwich ELISA diagnostic assay for the diagnosis of Neurocysticercosis (NCC) patients.

Example 2: Preparation of the Sandwich Antigen ELISA Assay for the Detection of the PLRP Protein Development of sandwich ELISA assay was carried out through different bioinformatics software's which were applied to the PLRP antigen, and the highly antigenic fraction sequences selected were used to obtain antibodies which could be used for the development of immunodiagnostic assay. Sandwich ELISA assay for detection of novel antigen PLRP to diagnose active disease in neurocysticercosis patients was developed and validated.

i. Preparation of ELBA

Sandwich Antigen ELISA as exemplified by the present invention was performed on two sets of samples—serum and urine Polystyrene microtiter plates (Maxisorp, Nunc) were coated with 100 μl capture antibody TsPP 21 in carbonate bicarbonate buffer, at pH 9.6 per well & incubated at 37° C. for 1 hr with continuous shaking and then kept at 4° C. for ON, Plate was sealed with a cover. Unbound antibodies were removed by washing buffer (PBS containing Tween20 0.05%) and the plate was tapped on blotting paper to remove residual buffer, free sites were blocked with blocking buffer 2% BSA for 2 h at 37° C. Test samples were tested in duplicate, added and incubated for 2 h at 37° C. and then washed with washing buffer. Biotinylated detection antibody 100 μl TsPP 22 was added and incubated at 37° C. for 1 hr followed by washing with PBST, extravidin horseradish peroxidase (sigma E2886) was added in 0.5% BSA PBS-T20 and incubated for 1 h at 37° C. followed by washing with PBST. TMB substrate was added & incubated for 15 min at 37° C. The reaction was stopped by adding 50 μl of 2N H2SO4. The plate was read using a spectrophotometer at 450 nm.

ii. Analysis of the Data

The data was analyzed by applying statistical software Graphpad prism 5 and Medcalc online. All statistical tests were two-tailed, P values≤0.5 were considered significant. All samples were tested in duplicate to give average absorbance value. Cut off values for ELISA were determined by mean O.D values+2S.D of ten serum/urine samples from healthy controls. ELISA positive test sera/urine had absorbances that were equal to or greater than the cutoff. The results were analyzed for statistical significance by calculating the sensitivity, specificity and other values. The relationship between sensitivity and specificity was obtained by determining Receiver operator statistics curve (ROC).

iii. Results

ELISA was performed on two set of samples—serum and urine (FIGS. 12A and 12B), it was observed that in serum samples 73 out of 103 samples were positive with a cut off O.D of 0.197. Among positive samples 24(28) were vesicular, 47(70) were colloidal. The sensitivity in vesicular samples was 85.71% (Table 2), while total sensitivity of the claimed ELISA serum was 70.87% with a specificity of 77.50% (Table 4). Further, it was observed that PLRP level was significantly higher (P≤0.0021) in patients as compared to controls (FIG. 13).

TABLE 2

ELISA (Serum) validation in different stages

| | Cases(Serum samples) | | | | |
|---|---|---|---|---|---|
| | All cases n = 103) | IP − NCC (n = 86) | EP − NCC EP + IP-NCC (n = 17) | Controls (n = 40) | p Value for Cases V/S Controls |
| Age, y, median (I) | 26 (20) | 24 (21.50) | 35 (13) | — | — |
| | | Sex, n (%) | | | |
| Male | 67 (65) | 57 (66.28) | 10 (58.82) | — | — |
| Female | 36 (35) | 29 (33.72) | 7 (41.18) | — | — |
| | | Symptoms, n (%) | | | |
| Headache | 52 (50.48) | 43 (50) | 9 (52.94) | — | — |
| Altered Sensorium | 14 (13.59) | 9 (10.46) | 5 (29.41) | — | — |
| Seizures | 86 (83.49) | 73 (84.88) | 13 (76.47) | — | — |
| | | Cyst stage and burden, n (%) | | | |
| 1. Vesicular cyst stage | 28 (27.18) | 20 (23.26) | 8 (47.05) | — | — |
| Solitary | 11 (10.68) | 10 (11.63) | 1 (5.88) | — | — |
| Multiple | 17 (16.50) | 10 (11.63) | 7 (41.17) | — | — |
| Positive | 24 (23.30) | 17 (19.76) | 7 (41.17) | — | — |
| Sensitivity, %(CI) | 85.71 (67.3-95.9) | 85 (62.1-96.8) | 87.5 (47.4-99.7) | — | <0.0010 |
| 2. Colloidal/nodular cyst stage | 70 (67.96) | 62 (72.09) | 8 (47.06) | — | — |
| Solitary | 46 (44.66) | 44 (51.16) | 2 (11.76) | — | — |
| Multiple | 24 (23.30) | 18 (20.93) | 6 (35.29) | — | — |
| Positive | 47 (45.63) | 41 (47.67) | 6 (35.29) | — | — |
| Sensitivity, %(CI) | 67.14 (54.9-77.9) | 66.13 (53-77.67) | 75 (34.9-96.8) | — | <0.0027 |
| 3. Calcified cyst stage | 4 (3.88) | 4 (4.65) | 0 (0) | — | — |
| Solitary | 1 (0.97) | 1 (1.16) | 0 (0) | — | — |
| Multiple | 3 (2.91) | 3 (3.49) | 0 (0) | — | — |
| Positive | 2 (1.94) | 2 (2.32) | 0 (0) | — | — |
| Sensitivity, %(CI) | 50 (6.76-93.24) | 50 (6.76-93.24) | 0 (0) | — | — |
| 4. Racemose cyst stage | 1 (0.97) | 0 (0) | 1 (5.88) | — | |
| Solitary | 0 (0) | 0 (0) | 0 (0) | — | — |
| Multiple | 1 (0.97) | 0 (0) | 1 (5.88) | — | — |
| Positive | 0 (0) | 0 (0) | 0 (0) | — | — |
| Sensitivity, %(CI) | 0 (0) | 0 (0) | 0 (0) | — | — |

1. Sensitivity and specificity have been calculated at 95% Confidence Interval (CI)

2. Abbreviations: IP-NCC = Intra-parenchymal neurocysticercosis; EP-NCC = Extra-parenchymal neurocysticercosis; EP + IP-NCC = Patients having both Extra-parenchymal & Intraparenchymal neurocysticercosis; I = Interquartile range, n = number of participants In Serum sample:

O.D. value of less than 0.197—Negative, No significant level of PLRP antigen detected.

O.D. value of more than 0.197—Positive, PLRP antigen to neurocysticercosis detected, which suggests current infection.

In Urine samples, 44 out of 59 samples were positive with a cut off O.D of 0.278. Among positive samples 13(17) were vesicular, 30(40) were colloidal. The sensitivity in vesicular samples was 76.5% and 75% in colloidal samples (Table 3), while total sensitivity of our urine ELISA was 74.6% with a specificity of 69.7% (Table 4). PLRP level was significantly high (P≤0.0001) in patients urine samples (FIG. 14).

In Urine Sample:

O.D. value of less than 0.278—Negative, No significant level of PLRP antigen detected.

O.D. value of more than 0.278—Positive, PLRP antigen to neurocysticercosis detected, which suggests current infection.

TABLE 3

ELISA (Urine) validation in different stages

| | Cases(Urine samples) | | | | |
|---|---|---|---|---|---|
| | All cases (n = 59) | IP − NCC (n = 51) | EP − NCC EP + IP-NCC (n = 8) | Controls (n = 33) | p Value for Cases V/S Controls |
| Age, y, median (I) | 24 (21.50) | 21 (18) | 34.5 (7.75) | — | — |
| | | Sex, n (%) | | | |
| Male | 44 (74.58) | 37 (72.55) | 7 (87.5) | — | — |
| Female | 15 (25.42) | 14 (27.45) | 1 (12.5) | — | — |
| | | Symptoms, n (%) | | | |
| Headache | 30 (50.85) | 27 (52.94) | 3 (37.5) | — | — |
| Altered Sensorium | 12 (20.34) | 8 (15.69) | 4 (50) | — | — |
| Seizures | 48 (81.36) | 42 (82.35) | 6 (75) | — | — |

TABLE 3-continued

ELISA (Urine) validation in different stages

| | Cases(Urine samples) | | | | |
|---|---|---|---|---|---|
| | All cases (n = 59) | IP − NCC (n = 51) | EP − NCC EP + IP-NCC (n = 8) | Controls (n = 33) | p Value for Cases V/S Controls |
| Cyst stage and burden, n (%) | | | | | |
| 1. Vesicular cysts stage | 17 (28.80) | 14 (27.46) | 3 (37.5) | — | — |
| Solitary | 7 (11.85) | 7 (13.73) | 0 (0) | — | — |
| Multiple | 10 (16.95) | 7 (13.73) | 3 (37.5) | | — |
| Positive | 13 (22.03) | 11 (21.57) | 2 (25) | — | — |
| Sensitivity, %(CI) | 76.5 (50.1-93.2) | 78.6 (49.2-95.3) | 66.7 (9.4-99.2) | — | <0.0011 |
| 2. Colloidal/nodular cysts stage | 40 (67.8) | 36 (70.59) | 4 (50) | — | — |
| Solitary | 26 (44.07) | 25 (49.02) | 1 (12.5) | — | — |
| Multiple | 14 (23.73) | 11 (21.57) | 3 (37.5) | — | — |
| Positive | 30 (50.85) | 26 (50.98) | 4 (50) | — | — |
| Sensitivity, %(CI) | 75 (58.8-87.3) | 72.2 (54.8-85.8) | 100 (39.8-100) | — | <0.0001 |
| 3. Calcified cysts Stage | 1 (1.7) | 1 (1.96) | 0 (0) | — | — |
| Solitary | 0 (0) | 0 (0) | 0 (0) | — | — |
| Multiple | 1 (1.7) | 1 (1.96) | 0 (0) | — | — |
| Sensitivity, %(CI) | 0 (0-97.5) | 0 (0-97.5) | 0 (0) | — | — |
| 4. Racemose cysts Stage | 1 (1.7) | 0 (0) | 1 (12.5) | — | — |
| Solitary | 0 (0) | 0 (0) | 0 (0) | — | — |
| Multiple | 1 (1.7) | 0 (0) | 1 (12.5) | — | — |
| Positive | 1 (1.7) | 0 (0) | 1 (12.5) | — | — |
| Sensitivity, %(CI) | 100 (2.5-100) | 0 (0) | 100 (2.5-100) | — | — |

1. Sensitivity and specificity have been calculated at 95% Confidence Interval (CI)

2. Abbreviations: IP-NCC = Intra-parenchymal neurocysticercosis; EP-NCC = Extra-parenchymal neurocysticercosis; EP + IP-NCC = Patients having both Extra-parenchymal & Intraparenchymal neurocysticercosis; I = Interquartile range; n = number of participants.

TABLE 4

ELISA results and validity of assay in Serum & Urine

| | Serum sample cases (n = 103) | | | | | |
|---|---|---|---|---|---|---|
| | All cases (n = 103) | IP-NCC(n = 86) | EP-NCC & EP + IP-NCC (n = 17) | Controls (n = 40) | p value for Controls V/s Patients | p value for Control V/s IP-NCC& EP + IP-NCC |
| ELISA Serum results, n (%) | | | | | | ⇩ |
| Positive | 73 (70.9) | 60 (69.77) | 13 (76.47) | 9 (22.5) | — | IP: <0.0027 |
| Negative | 30 (29.1) | 26 (30.23) | 4 (23.53) | 31 (77.5) | — | EP: <0.0013 |
| Solitary | 58 (56.31) | 55 (63.95) | 3 (17.65) | — | — | |
| Sensitivity, % | 74.14 (60.9-84.7) | 74.55 (61.0-85.3) | 66.67 (9.4-99.2) | — | <0.003 | |
| Multiple | 45 (43.69) | 31 (36.04) | 14 (82.35) | — | — | |
| Sensitivity, % | 66.67 (51.1-80) | 61.29 (42.2-78.2) | 78.57 (49.2-95.3) | — | <0.002 | |
| Validity ELISA Serum | | | | | | |
| Sensitivity, % | 70.87 (61.1-79.4) | 69.8 (58.9-79.2) | 76.5 (50.1-93.2) | — | <0.0021 | |
| Specificity, % | 77.50 (61.6-89.2) | 77.50 (61.6-89.2) | 77.50 (61.6-89.2) | — | — | |

| | Urine sample cases (n = 59) | | | | | |
|---|---|---|---|---|---|---|
| | All cases (n = 59) | IP-NCC(n = 51) | EP-NCC & EP + IP-NCC (n = 8) | Controls (n = 33) | p value for Controls V/s Patients | p value for Control V/s IP-NCC& EP + IP-NCC |
| ELISA Urine results, n (%) | | | | | | ⇩ |
| Positive | 44 (74.57) | 37 (72.55) | 7 (87.5) | 10 (30.3) | — | IP: <0.0001 |
| Negative | 15 (25.43) | 14 (27.45) | 1 (12.5) | 23 (69.7) | — | EP: <0.0044 |
| Solitary | 33 (55.94) | 32 (62.74) | 1 (12.5) | — | — | |
| Sensitivity, % | 72.73 (54.5-86.7) | 71.88 (53.3-86.3) | 100 (2.5-100) | — | <0.0001 | |
| Multiple | 26 (44.06) | 19 (37.26) | 6 (75) | — | — | |
| Sensitivity, % | 76.92 (56.4-91) | 73.68 (48.8-90.9) | 85.71 (42.1-99.6) | — | <0.0015 | |

TABLE 4-continued

ELISA results and validity of assay in Serum & Urine

| Validity ELISA Urine | | | | | |
|---|---|---|---|---|---|
| Sensitivity, % | 74.6 (61.5-85) | 72.55 (58.3-84.1) | 87.5 (47.3-99.7) | — | <0.0001 |
| Specificity, % | 69.7 (51.3-84.4) | 69.7 (51.3-84.4) | 69.7 (51.3-84.4) | — | — |

Data from previous studies-Sensitivity and specificity of ELISA (S. R. V. Atluri et al., 2009)

| ELISA | CSE Serum | Urine | ES Serum | Urine | LMM Serum | Urine |
|---|---|---|---|---|---|---|
| Sensitivity | 38.4 | 46.4 | 63.2 | 44 | 30.4 | 47.2 |
| Specificity | 88 | 66.4 | 76.8 | 65.2 | 85.6 | 58.4 |

1. Sensitivity and specificity have been calculated at 95% Confidence Interval (CI)
2. Abbreviations: IP-NCC = Intra-parenchymal neurocysticercosis; EP-NCC = Extra-parenchymal neurocysticercosis; EP + IP-NCC = Patients having both Extra-parenchymal & Intraparenchymal neurocysticercosis; n = number of participants; CSE = crude soluble extract; ES = excretory secretory antigen; LMM = low molecular mass antigen.

Sensitivity among extraparenchymal cases was 76.5% and 87.5% respectively among serum and urine samples and 69.8% and 72.55% in intraparenchymal cases. The sensitivity of serum and urine samples in solitary lesion cases was 74.14% and 72.73% respectively. In contrast, in multiple lesion cases the sensitivity was 66.67% and 76.92% in serum and urine samples respectively. In previous studies, sensitivity of ELISA in different antigens is 30.4-63.2% in serum and 44-47.2% in urine which is significantly lower than the methods of the present invention and secondly no continuous supply of parasitic material is required in the present invention (S. R. V. Atluri et al., 2009).

Diagnostic odds ratio (DOR) of serum and urine ELISA was 8.389 and 6.747 respectively, ELISA serum PPV was 89.02% and NPV was 50.82%, ELISA urine PPV was 81.49% and NPV was 60.55%. ROC curve is more towards Y-axis (FIG. 15), which indicates that PLRP detection of antigen is more accurate.

In conclusion, the developed ELISA assay of the present invention demonstrates results with high sensitivity and specificity as compared to other techniques. Further, the exemplified assay of the present invention can be easily used in institutions and areas where sophisticated infrastructure is not available to differentiate between active and inactive infection. In cases, which have non characteristic images in CT & MRI this test will help in definitive diagnosis. Thus, PLRP positive detection will be an indicator of active NCC and this distinction between active and inactive NCC is more significant in clinical terms than the distinction between NCC and no NCC, since the presence or absence of live cysts can affect treatment decisions. The exemplified Ag-ELISA test has the ability to detect the existence of living cysts, making it a distinctive test.

Advantages

1. Simple and economical method for detecting live infection than other immunoassays and neuroimaging methods.
2. Low-cost kit.
3. Minimally invasive method as serum and urine samples can be easily collected.
4. Does not require hospitalization and user friendly.
5. Patient may not face irrelevant cysticercidal therapy because this test will differentiate between active and inactive cases due to drop in antigen level, useful for follow up after treatment, also reduces misdiagnosis which saves from drug overuse and from disability adjusted years in life.
6. Antibody-based testing does not need the use of parasites.
7. It can detect even mild active infection so it can be used for active prevalence studies in animals which cannot be detected by visual inspection.
8. Endemicity can be controlled and it can be used to test the efficacy of vaccine by inspection in orally challenged animals with viable cysticerci.

We claim:

1. A peptide consisting of a sequence of SEQ ID NO: 2 or SEQ ID NO: 3.

2. A composition comprising the peptide of claim 1.

* * * * *

SEQUENCE LISTING

```
Sequence total quantity: 3
SEQ ID NO: 1            moltype = AA  length = 219
FEATURE                 Location/Qualifiers
source                  1..219
                        mol_type = protein
                        organism = Taenia sp.
SEQUENCE: 1
MKGKMTIGAV SEPSKKHKKS SEFGNGGQAT EEGSQPSGRK RKTRPTESNE SRATEVITEA  60
EAFRPTKRRK KSLEVAIDST EERKAVSHWQ QKSERDLEKS KKNVTETKKP ESVKKSVKFA  120
DELVAPRSLP KNKSKTSILK VSTPSVKASN ENSGVEKANE ADGNGTETKA RKPKKSKNAL  180
KRIRWVKRHH KKTFSRRQRR ANRELARSRP QRDAEQHLA                         219

SEQ ID NO: 2            moltype = AA  length = 20
FEATURE                 Location/Qualifiers
source                  1..20
                        mol_type = protein
                        organism = Taenia sp.
SEQUENCE: 2
CSQPSGRKRK TRPTESNESR                                              20
```

```
SEQ ID NO: 3            moltype = AA  length = 20
FEATURE                 Location/Qualifiers
source                  1..20
                        mol_type = protein
                        organism = Taenia sp.
SEQUENCE: 3
RQRRANRELA RSRPQRDAEC                                            20
```